United States Patent [19]

Lennox

[11] Patent Number: 5,122,137
[45] Date of Patent: Jun. 16, 1992

[54] TEMPERATURE CONTROLLED RF COAGULATION
[75] Inventor: Charles D. Lennox, Hudson, N.H.
[73] Assignee: Boston Scientific Corporation, Watertown, Mass.
[21] Appl. No.: 515,850
[22] Filed: Apr. 27, 1990
[51] Int. Cl.⁵ .............................. A61B 17/39
[52] U.S. Cl. ...................... 606/40; 606/42; 606/49; 128/401; 128/804
[58] Field of Search .................... 606/33–40, 606/41, 47; 128/736, 804, 399–401

[56] References Cited

U.S. PATENT DOCUMENTS

| | | |
|---|---|---|
| 1,885,106 | 11/1932 | Briggs . |
| 3,634,652 | 1/1972 | Shimizu et al. .......... 606/40 X |
| 3,798,967 | 3/1974 | Gieles et al. . |
| 3,895,635 | 7/1975 | Justus et al. . |
| 3,960,141 | 6/1976 | Bolduc . |
| 4,071,028 | 1/1978 | Perkins . |
| 4,092,986 | 6/1978 | Schneiderman . |
| 4,121,590 | 10/1978 | Gonser . |
| 4,126,137 | 11/1978 | Archibald . |
| 4,142,529 | 3/1979 | Letenser et al. . |
| 4,160,455 | 7/1979 | Law . |
| 4,196,734 | 4/1980 | Harris . |
| 4,204,549 | 5/1980 | Paglione . |
| 4,217,910 | 8/1980 | Khalil . |
| 4,227,535 | 10/1980 | Connor . |
| 4,228,809 | 10/1980 | Paglione ................ 128/804 |
| 4,240,441 | 12/1980 | Khalil . |
| 4,303,073 | 1/1981 | Archibald . |
| 4,311,154 | 1/1982 | Sterzer et al. . |
| 4,346,716 | 8/1982 | Carr . |
| 4,397,314 | 8/1983 | Vaguine . |
| 4,446,874 | 5/1984 | Vaguine . |
| 4,449,528 | 5/1984 | Auth et al. . |
| 4,522,194 | 6/1985 | Normann . |
| 4,543,090 | 9/1985 | McCoy . |
| 4,574,801 | 3/1986 | Manes . |
| 4,580,562 | 4/1986 | Goof et al. . |
| 4,582,057 | 4/1986 | Auth et al. . |
| 4,587,975 | 5/1986 | Salo et al. . |
| 4,612,940 | 9/1986 | Kasevich . |
| 4,646,737 | 3/1987 | Hussein . |
| 4,662,368 | 5/1987 | Hussein . |
| 4,672,962 | 6/1987 | Hershenson . |
| 4,685,459 | 8/1987 | Koch et al. ............ 606/40 X |
| 4,695,697 | 9/1987 | Kosa . |
| 4,754,752 | 7/1988 | Ginsburg et al. . |
| 4,955,377 | 9/1990 | Lennox et al. ............ 128/401 |

OTHER PUBLICATIONS

Werts et al., "Thermistor Artifacts Using the MA-251 Microwave Interstitial Antenna" (abstract), 1988.
Astrahan et al., Temp. Meas. from MW Antenna, Mar. 3, 1988, pp. 23–25.
Brezovich et al, A Practical System for Clinical Radiofrequency Hyperthermia, Mar. 1981, pp. 423–443.
Gilbert et al., Nonsurgical Management of Acute Nonvariceal Upper Gastrointestinal Bleeding, pp. 349–395.
Haines et al., Tissue Heating During Radiofrequency Catheter Ablation, Jun. 1989, pp. 962–973.
Loshek, Pulsed Microwave Thermometry, 1980, pp. 517–519.
The Luxtron Corp., Small Business Innovation Research Program, 1984, pp. 1–4.
Protell et al., The Heater Probe, 1978, p. 257.
Samaras, Correction of Microwave-Induced Thermistor Sensor Errors, 1983, pp. 326–332.
Szwarnowski, A Thermometer for Measuring Temperatures in the Presence of Electromagnetic Fields, 1983, pp. 79–84.
Zeiher et al. A Prototype RF-Heated "Hot Balloon" PTCA-Catheter, Oct., 1988, Article 1181.

*Primary Examiner*—Stephen C. Pellegrino
*Assistant Examiner*—Steven J. Shumaker
*Attorney, Agent, or Firm*—Fish & Richardson

[57] ABSTRACT

Radiofrequency medical devices for ohmic heating of tissue of a patient include a temperature sensor carried by and in thermally conductive relationship with a thermally conductive electrode. The sensor is connected for feedback to a control circuit that modulates RF power applied to the electrode according to the signal received from the temperature sensor. The control circuit and RF power supply alternate between two operating modes. In the first mode the RF power supply applies RF power to the electrode. In the second mode the control circuit senses a signal from the temperature sensor in the absence of RF signal. The control circuit compares the signal from the temperature sensor to a set value and modulates the RF power applied to the electrode in accordance with the set value.

21 Claims, 6 Drawing Sheets

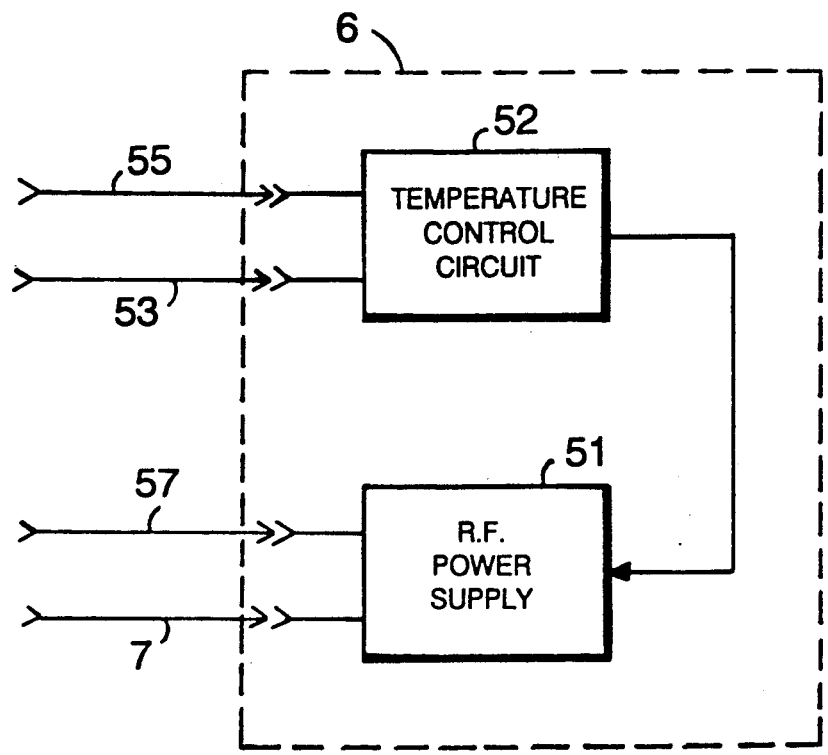
FIG. 10
FIG. 11
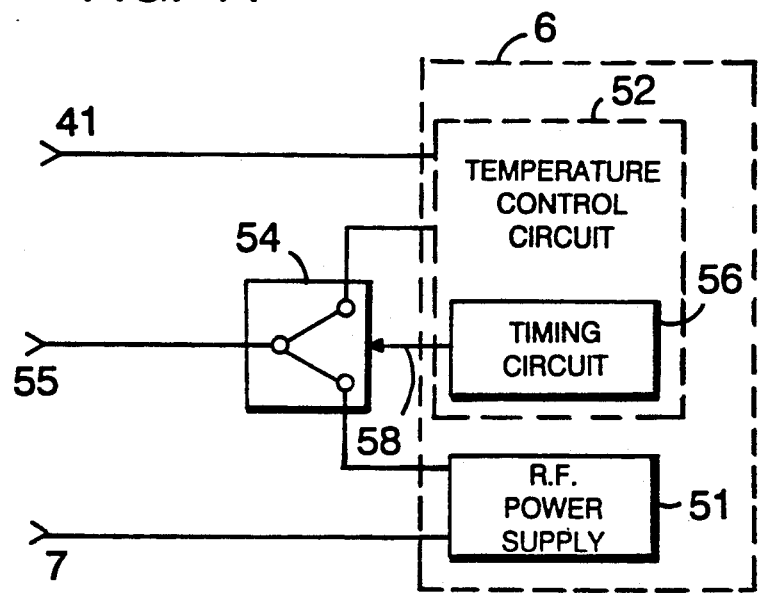

TEMPERATURE CONTROLLED RF COAGULATION

BACKGROUND OF THE INVENTION

This invention relates to medical devices that apply an RF electrical current to tissue of a patient in order to heat the tissue to induce coagulation.

Devices that perform localized heating of tissue may apply an RF electrical current through the tissue by means of electrical contacts. Tissue in the vicinity of an electrical contact is heated through resistance of the tissue to the electrical current. Such tissue heating devices may typically apply current having an intensity and duration that is empirically calculated to heat the tissue to a desired temperature. Nevertheless, the actual extent of heating is unpredictable. Excessive heating of the tissue can cause complete desiccation or "charring" of the tissue that surrounds one or more electrical contacts. A film of charred tissue around an electrical contact can result in a high impedance between the electrical contacts that in turn leads to a cessation of the heating process. Moreover, excessive heating of the tissue can cause an electrical contact to stick to the tissue.

SUMMARY OF THE INVENTION

The invention features a radiofrequency medical device for ohmic heating of tissue of a patient in order to induce coagulation. The device includes a plurality of RF conductors between which RF current flows for tissue-coagulation. At least one of the conductors is a thermally conductive electrode that concentrates RF current in a local region of tissue contacted by the electrode. The electrode is connected to one pole of an RF power supply. A second pole of the RF power supply is connected to the patient via a second conductor. A temperature sensor is carried by and in thermally conductive relationship with the thermally conductive electrode. The temperature sensor senses the temperature of the electrode, and thereby indirectly senses the temperature of tissue in contact with the electrode. The sensor is connected by a feedback line to a control circuit that automatically modulates RF power applied to the electrode according to the feedback signal received from the temperature sensor. The control circuit and RF power supply alternate between two operating modes. In the first mode the RF power supply applies RF power to the electrode. In the second mode the control circuit senses a signal from the temperature sensor in the absence of RF signal. The control circuit compares the signal from the temperature sensor to a set value and modulates the RF power applied to the electrode in accordance with the set value.

In preferred embodiments, the temperature sensor is a thermistor. Alternatively, the temperature sensor may be a thermocouple. The period of temperature sensing is of the order of 1 percent of the cycle time, and the frequency of the cycle is substantially greater than the frequency response of the electrode-tissue system. The set value is a user set reference signal internal to the control circuit. The control circuit modulates RF power applied to the electrode to cause the temperature of the temperature sensor to approach a temperature represented by the reference signal, thereby to control the temperature of the electrode and consequently the temperature of tissue contacted by the electrode. The second conductor is a patient grounding plate. The control circuit modulates the RF power applied to the electrode by varying intensity of the RF power rather than by disconnecting the RF power during the first mode.

In one embodiment the conductors are opposed electrodes mounted on opposing jaws of a forceps, each of which has a localized contact with the tissue of the patient. Each of the electrodes may be contacted by a temperature sensor monitored by the control circuit, the RF voltage being modulated in accordance with the higher temperature that is sensed by a respective sensor. In another embodiment the electrode is constructed for thermal ablation therapy for arrhythmias, and the thermistor is embedded into the electrode. In another embodiment the electrode is mounted on a probe for gastro-intestinal hemostasis. In another embodiment the electrode is mounted on a cautery probe. In another embodiment the electrode is the tip of a guidewire probe for thermally occluding fallopian tubes or seminal ducts. The guidewire probe is coated with insulation except at a tip of the probe, and the thermistor is mounted in the tip of the guidewire probe. In another embodiment the electrode is the tip of a needle for percutaneous electrode coagulation treatment of liver metastases or for transrectal electrode coagulation treatment of prostatic tumors.

The invention provides a new, feedback-controlled, time-sharing way of regulating coagulation induced by $I^2R$ losses of RF current through tissue. Since the RF current is most concentrated at the location of the electrode, the tissue in the immediate vicinity of the electrode is heated more than other tissue. The electrode thermally conducts heat from the tissue, and therefore the temperature of the electrode closely approximates the temperature of the tissue contacting the electrode. Thus invention takes advantage of this feature by providing a temperature sensor that, in the absence of interfering rf currents, detects and, by feedback, controls the temperature of the electrode, as an indirect means of measuring and controlling the temperature of tissue contacting the electrode. The configuration in which the temperature sensor is carried by the electrode provides simplicity of construction and use.

DESCRIPTION OF THE PREFERRED EMBODIMENTS

We first briefly describe the drawings.

DRAWINGS

FIG. 10 is a block diagram of the RF power supply and temperature control circuitry of the embodiments of the invention shown in FIGS. 1, 3, 7, 8, and 9.

FIG. 11 is a block diagram of the RF power supply and temperature control circuitry of the embodiment of the inventions shown in FIG. 5.

STRUCTURE

Figure 1:
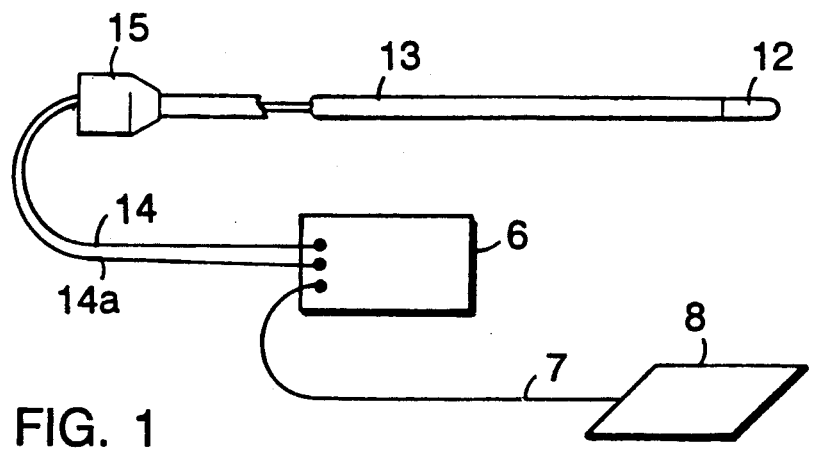
FIG. 1 is a drawing of an RF probe according to the invention, useful for gastro-intestinal hemostasis.

FIG. 1 shows an RF probe according to the invention, used for gastro-intestinal hemostasis. A catheter shaft 13 has an RF electrode 12 mounted at its tip. Catheter shaft 3 has a diameter of 7 French, and is sized to be inserted through the working channel of an endoscope. RF electrode 12 includes a thermistor assembly. A cable 14 for the RF electrode and a two-conductor cable 14a for the thermistor pass through cable strain relief 15 and connect with RF power supply and controller 6. Another cable 7 connects RF power supply and controller 6 with patient grounding plate 8.

Figure 2:
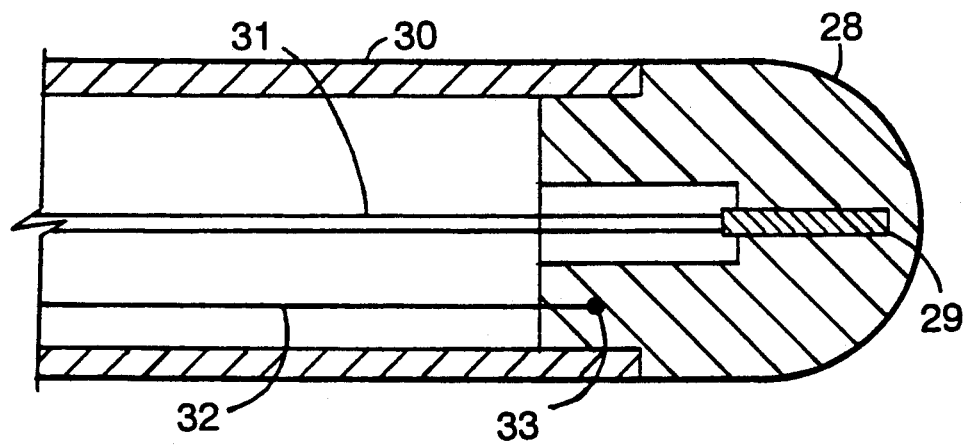
FIG. 2 is a lengthwise cross-sectional drawing of the RF electrode of the RF probe of FIG. 1.

Referring to FIG. 2, the RF electrode of the device shown in FIG. 1 includes a platinum electrode portion 28 mounted on catheter shaft tip 30. A pair of thermistor leads 31 connect with thermistor assembly 29, which is embedded within platinum electrode portion 28 in thermal contact therewith. Thermistor assembly 29 senses the temperature of electrode portion 28, as an indirect indication of the temperature of the tissue surrounding the electrode. Note that the temperature of the tissue immediately surrounding the electrode is ordinarily the highest temperature in the system, because the current 30 density through the tissue is highest at the electrode-tissue interface. A single RF electrode lead 32 connects with electrode portion 28 at resistance weld 33.

Figure 3:
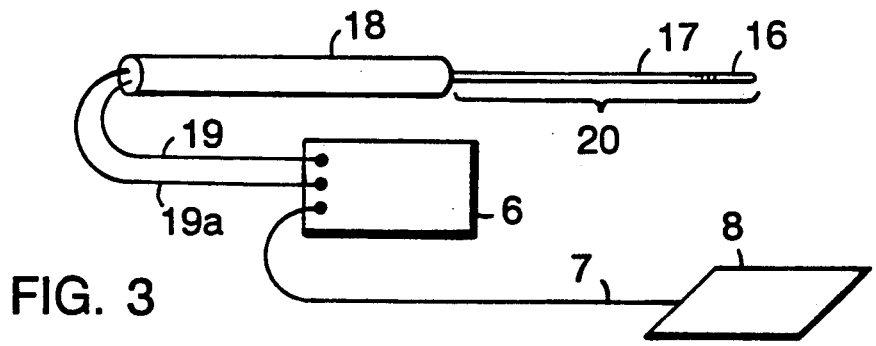
FIG. 3 is a drawing of a hand-held surgical hemostasis probe according to the invention, or of a needle probe according to the invention useful for percutaneous electrode coagulation treatment of liver metastases or prostatic tumors.

FIG. 3 shows an RF probe according to the invention, used as a hand-held surgical hemostasis probe, or as a needle probe for percutaneous electrode coagulation treatment of liver metastases or for transrectal electrode coagulation treatment of prostatic tumors to cause thermal ablation of the prostatic tumor. A probe handle 18 attaches to a platinum hypo-tube probe 20 having an insulated section 17 and a non-insulated electrode section 16. A cable 19 for the RF electrode and a two-conductor cable 19a for the thermistor connect with RF power supply and controller 6. Another cable 7 connects RF power supply and controller 6 with patient grounding plate 8.

Figure 4:
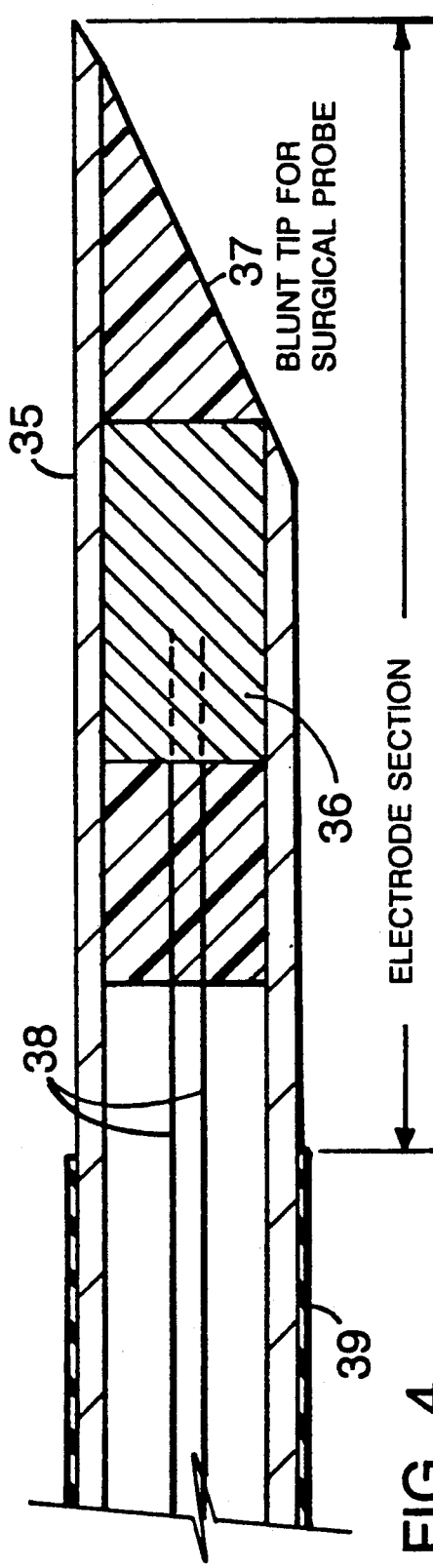
FIG. 4 is a lengthwise cross-sectional drawing of the electrode of the surgical probe or needle probe of FIG. 3.

Referring to FIG. 4, the electrode section of the RF probe of FIG. 3 includes a rigid, platinum hypodermic tube 35 that serves both as an RF electrode and as a conductor to the RF electrode. An electrical insulation coating 39 insulates all of hypodermic tube 35 except for the electrode section at the tip. A pair of thermistor leads 38 connect with thermistor assembly 36, which is embedded in an epoxy 37 inside hypodermic tube 35. As a needle probe, electrode section 16 (FIG. 3) includes the rigid, pointed tip shown. Alternatively, a percutaneous probe need not have a rigid, pointed tip if the probe is designed to follow a needle into a patient's body. As a surgical hemostasis probe, however, the electrode has a blunt tip (lengthwise cross-section of electrode rectangular).

Figure 5:
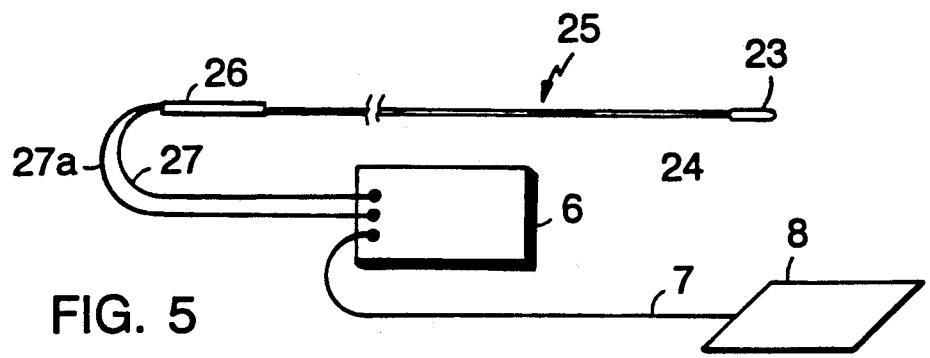
FIG. 5 is a drawing of a guidewire probe having a temperature-controlled tip electrode according to the invention, useful for fallopian tube ligation or seminal duct ligation.

FIG. 5 shows a guidewire probe according to the invention, which can be used for occluding fallopian tubes or seminal ducts, and which can also be used in coronary or peripheral arteries, urinary tracts, biliary tracts, and gastro-intestinal tracts. In the fallopian tube application, instead of ligation, in which an incision is usually made to access the fallopian tubes, the guidewire probe is inserted through the uterus and into the fallopian tube to heat the wall of the fallopian tube at a controlled temperature, thereby causing injury to the fallopian tube, and causing an inflammatory response and scarring to occlude the fallopian tube. The guidewire probe includes a flexible guidewire 25 that has an electrically insulated portion 24 and a non-insulated electrode tip portion 23. Guidewire 25 has a diameter of approximately 0.038 inches for urinary, and gastrointestinal tract applications, 0.025–0.038 inches for peripheral arteries, and 0.014–0.018 inches for coronary applications. Guidewire 25 typically has a length of 50–75 centimeters for applications in the seminal ducts or fallopian tubes, and a length of approximately 175 centimeters for coronary angioplasty procedures. At least a portion of the distal region of the guidewire is radiopaque. Accordingly, the guidewire may be metal or may contain platinum rings. The outside portion of the guidewire is suitable for passage of a catheter device over the exterior of the guidewire. In addition to coagulation, guidewire 25 provides a guiding function, and serves to probe through occlusions and fatty tissue. A cable 27 for the RF electrode tip portion and a single-conductor cable 27a for the thermistor pass through conductor strain relief 26 and connect with RF power supply and controller 6. Another cable 7 connects RF power supply and controller 6 with patient grounding plate 8.

Figure 6:
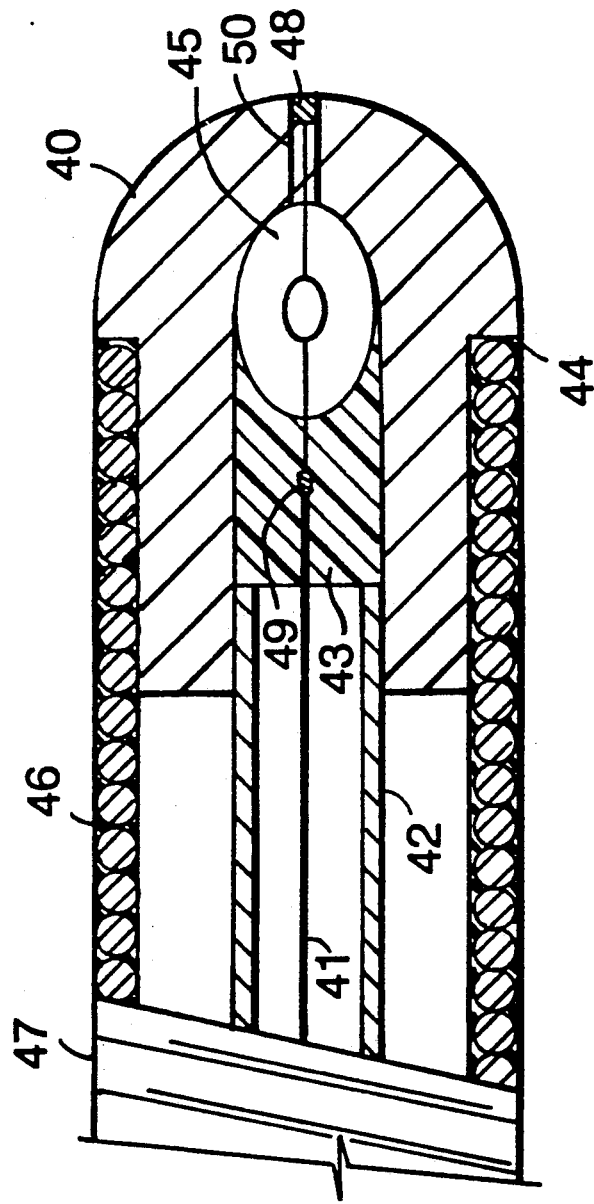
FIG. 6 is a lengthwise cross-sectional drawing of the electrode of the guidewire probe of FIG. 5.

Referring to FIG. 6, the RF electrode tip portion of the guidewire 25 of FIG. 5 includes a platinum RF electrode 40 that is mounted at the tip of a guidewire coil 47 that serves as an RF conductor to electrode 40. A resistance weld 44 electrically connects guidewire coil 47 with electrode 40. Guidewire coil 47 is covered by an electrical insulation coating 46. Epoxy 43 cements a thermistor bead 45 within electrode 40. A single conductor 41 passes through polyamide tubing 42 within the guidewire and connects with a lead of thermistor bead 45 at resistance weld 49. Another thermistor lead 50 connects with electrode 40 at resistance weld 48.

Figure 7:
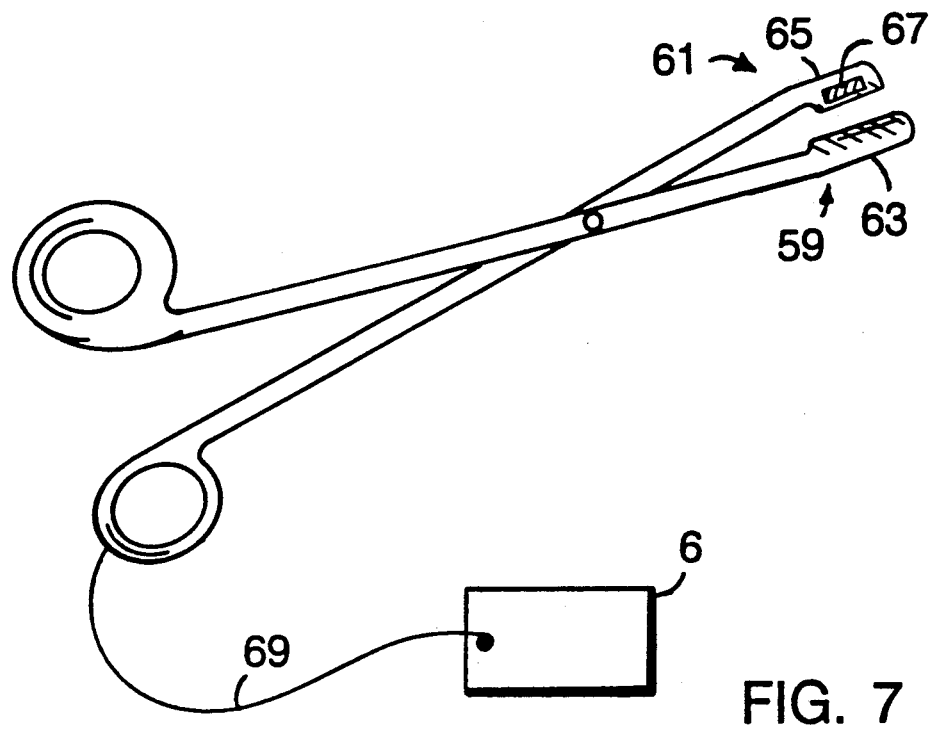
FIG. 7 is a drawing of a forceps device that includes a temperature-controlled RF electrode according to the invention.

FIG. 7 shows a forceps device according to the invention. The forceps device includes a pair of platinum prongs 59 and 61. Prong 59 has a greater area of contact with tissue than prong 61. Embedded within prongs 59 and 61 are electrodes 63 and 65 respectively. A thermistor 67 is embedded within the prong 61 having the smaller area of contact with tissue. Thermistor 67 is positioned in intimate contact with electrode 65. A two-conductor cable 69, which includes a conductor attached to electrode 63 and a conductor attached to electrode 65, and a two-conductor cable 69a for thermistor 67, connect with RF power supply and controller 6. The conductor that is attached to electrode 63 may cross from one part of the forceps to the other at, e.g., the pivot point.

Figure 8:
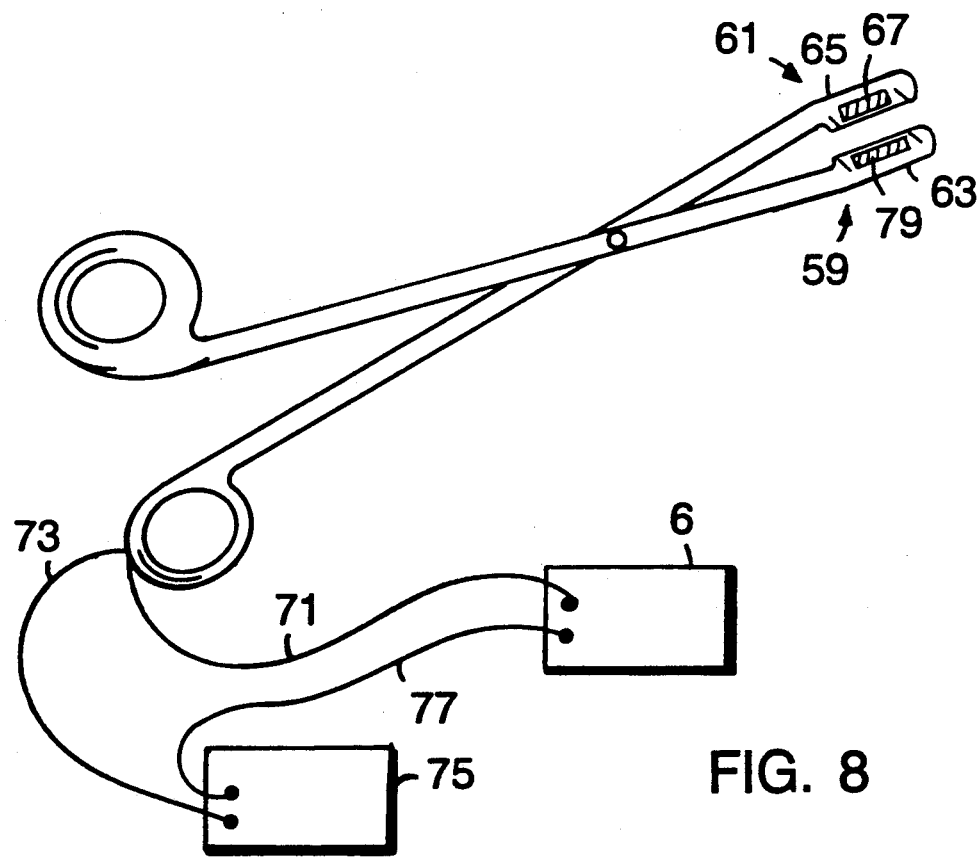
FIG. 8 is a drawing of a forceps device that includes a temperature-controlled RF electrode according to the invention in each prong of the forceps device.

FIG. 8 shows a forceps device according to the invention in which prongs 59 and 61 have approximately the same area of contact with tissue. Embedded within prongs 59 and 61 are thermistors 79 and 67 respectively. Thermistors 79 and 67 are positioned in intimate contact with electrodes 63 and 65 respectively. A two-conductor cable 71, which includes a conductor attached to electrode 63 and a conductor attached to electrode 65, connects with RF power supply and controller 6. A four-conductor cable 73, which includes two conductors attached to thermistor 67 and two conductors attached to thermistor 79, connects with a selection circuit 75, which selects the thermistor that sensed the highest temperature. A two-conductor cable 77 connects RF power supply and controller 6 with the thermistor selected by selection circuit 75.

Figure 9:
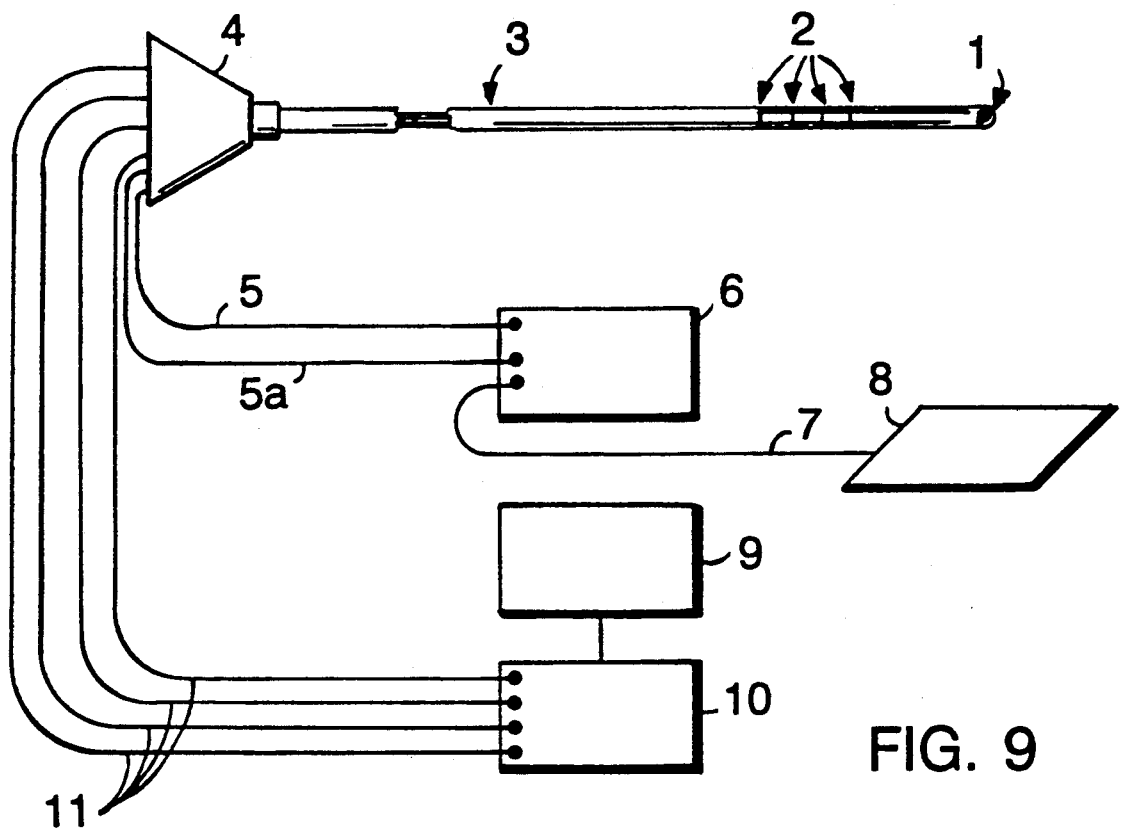
FIG. 9 is a drawing of an electro-physiology catheter, useful for cardiac arrythmia ablation therapy, that includes a temperature-controlled RF electrode according to the invention.

FIG. 9 shows an electro-physiology catheter according to the invention, used for thermal ablation for arrhythmias. The catheter includes a nylon extrusion catheter shaft 3 having a thermally conductive radio-frequency electrode 1 mounted at its tip. Electrode 1 has embedded within it a thermistor assembly. The details of the construction of the electrode and thermistor assembly are the same as those shown in FIG. 2. Electrode 1 has a diameter of 7 French. A cable 5 for the RF electrode and a two-conductor cable 5a for the thermistor pass through electrode lead strain relief 4 and connect with RF power supply and controller 6. Another cable 7 connects RF power supply and controller 6 with patient grounding plate 8. Catheter shaft 3 includes a series of electro-physiology electrodes 2 used to sense electrical impulses from the heart, in order to determine the location on the heart of a source of abnormal impulses, so that electrode 1 can be brought into contact with the location of the source of the abnormal impulses. A set of RF electrode leads 11 for the electro-physiology electrodes 2 passes through electrode lead strain relief 4 and connects with a standard electro-physiology switching system 9 that records data from electro-physiology electrodes 2 onto a chart recorder 10.

FIG. 10 shows a block diagram of the RF power supply and temperature control circuitry 6 of the RF probes shown in FIGS. 1, 3, 7, 8, and 9. RF power supply and temperature control circuitry 6 consists of RF power supply 51 and temperature control circuit 52. RF power supply 51 preferably operates at 650 kilohertz, but can be at any frequency within the range of about 100 kilohertz to over 100 megahertz. It is important to use radio frequency power rather than direct or low frequency current, or microwave power, because the risk of a physiological response or electrocution response is reduced at RF frequencies above 100 kHz kilohertz as compared with d.c. or low frequencies, and because microwave power would lead to radiative losses in the conductor wires that can result, e.g., in unwanted heating of the catheter shaft, probe, or guidewire.

Conductor 7 connects the patient grounding plate 8 (or one of the prongs of a forceps) with RF power supply 51. Conductors 53 and 55 connect the thermistor with temperature control circuit 52. Conductor 57 connects the electrode with RF power supply 51. The temperature sensing period is approximately 1 percent of the 60 hertz cycle. Because the duration of the temperature sensing period is relatively short compared with the power application period, the amount of power that must be applied to the tissue during the power application period in order to heat sufficiently the tissue within a given amount of time can be minimized. During the temperature sensing period, temperature control circuit 52 determines how much power, at maximum, RF power supply 51 should supply during the power application period. By thus time-sharing between temperature sensing and application of current to the electrode, the temperature control circuitry eliminates the possibility that RF noise will interfere with the signal from the temperature sensor.

FIG. 11 shows a block diagram of the RF power supply and temperature control circuitry 6 of the RF probe shown in FIG. 5. RF power supply and temperature control circuitry 6 consists of RF power supply 51, temperature control circuit 52, and solid state switch 54. Conductor 7 connects patient grounding plate 8 with RF power supply 51, and conductor 41 connects the thermistor with temperature control circuit 52. Timing circuit 56 of temperature control circuit 52 toggles hold/NOT sample line 58 so that solid state switch 54 toggles back and forth, whereby wire 55 functions alternately as a lead connecting RF power supply 51 with the electrode and as a lead connecting temperature control circuit 52 with the thermistor. (Recall that the electrode and the thermistor are electrically connected with each other in the embodiment of FIGS. 5 and 6. Wire 55 connects solid state switch 54 with guidewire coil 47, which in turn connects with electrode 40, and with thermistor 45 through electrode 40.) When solid state switch 54 connects wire 55 with temperature control circuit 52, temperature control circuit 52 determines how much power, at maximum, RF power supply 51 should supply when solid state switch 54 next connects wire 55 with RF power supply 51.

Figure 12:
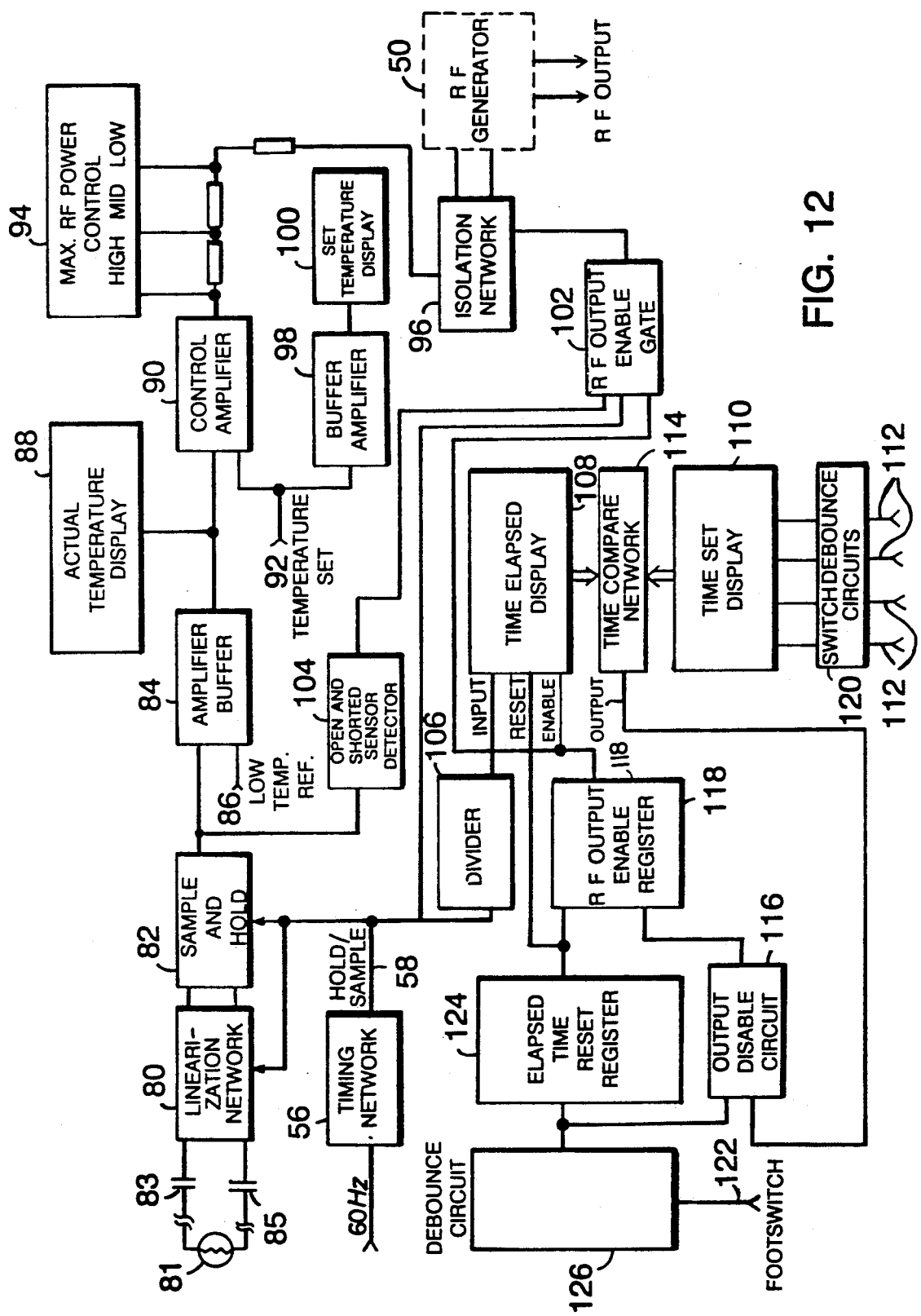
FIG. 12 is a detailed block diagram of the temperature control circuit shown in FIGS. 10 and 11.

Referring to FIG. 12, in temperature control circuit 52, the resistance of thermistor 81 decreases with increasing temperature. The resistance is measured by passing a known current through the sensor 81. The resultant voltage is then interpreted as a temperature value. Hence, this resistance measuring technique follows from the basis relationship of Ohm's Law, or V=IR. If I (current) is a known quantity and constant, then V (voltage) is proportional to R (the resistance of the sensor). Capacitors 83 and 85 from an isolation network. The capacitors isolate the sensor 81 from the remaining circuit by blocking direct current flow while allowing a short measuring pulse to pass through thermistor 81. An alternate method of direct current isolation is to replace the capacitors with an appropriately matched transformer.

Linearization network 80 includes a switched constant-current source that injects current into thermistor 81 in order to develop a temperature-related voltage across thermistor 81. Current injection is performed for a duration of 100 microseconds. Linearization network 80 linearizes the voltage across thermistor 81 to achieve a nearly linear (20 mv/degree) temperature signal from the nonlinear characteristics of the thermistor element 81.

Linearization network 80 delivers the linearized signal to sample and hold register 82. Sample and hold register 82, which consists of an amplifier element and a storage capacitor, is used to translate the short sensor resistance measurement into a continuous (D.C. voltage) temperature signal. The amplitude of the output of sample and hold register 82 is inversely related to the temperature of thermistor 81. The output of sample and hold register 2, which is a direct current voltage whose level decreases with temperature at a rate of 20 mv per degree centigrade in the working range of 20 to 100 degrees, is delivered to amplifier buffer 84 having low-temperature reference 86. Actual temperature display circuit 88 displays the output of amplifier buffer 84. Control amplifier 90 compares the output of amplifier buffer 84 with a temperature set voltage 92 that is set by the user. The temperature set voltage, which represents a temperature below the vaporization point or charring threshold of the tissue, is typically around 100° C. The maximum RF power control circuit 94 receives the output of control amplifier 90 and determines the level of RF power, at maximum, that the RF power supply 51 should produce. The signal from the maximum RF power control circuit 94 is received by isolation network 96, which interfaces with RF power supply 51. The temperature set voltage 92 is received by buffer amplifier 98 and displayed by set temperature display 100.

Timing circuit 56 toggles hold/NOT sample line 58 at 60 hertz. Hold/NOT sample line 58 is low during 1 percent of the cycle and high during the other 99 percent of the cycle. Hold/NOT sample line 58 is low when signals from temperature sensor 81 are being sampled and high when signals from temperature sensor 81 are not being sampled. Hold/NOT sample line 58 is received by RF output enable gate 102. The output of sample and hold register 82 is processed by open and short sensor detector 104 to determine whether a sensor malfunction, such as a shorted or open sensor, has occurred. The output of open and shorted sensor detector 104 is received by RF output enable gate 102. RF output enable gate 102 delivers a signal to isolation network 96, which turns off RF power supply 51 when there has been a sensor malfunction or when signals from the temperature sensor are being sampled.

Divider 106 receives hold/NOT sample line 58 and delivers its output to time elapsed display 108. Time set display 110 displays the time indicated by time set switches 112, which are set by the user. Time compare network 114 compares the elapsed time with the time set by the user, and delivers an output signal to output disable circuit 116. The output of output disable circuit 116, which is active only when the elapsed time is less than the time set by the user, is delivered to RF output enable register 118. RF output enable register 118 in turn delivers the signal to the enable input to time elapsed display 108, and also to RF output enable gate 102, so that RF power supply 51 may be turned off when the time set by the user has elapsed. Switch debounce circuits 120 are provided for time set switches 112.

The user must depress footswitch 122 in order for RF power supply 50 to operate. While footswitch 122 is activated, and while the elapsed time is less than the time set by the user, output disable circuit 116 delivers a signal to RF output enable register 118, which in turn delivers the signal to the enable input of time elapsed display 108, and also to RF output enable gate 102 so that RF power supply 51 may be turned on. Deactivation of footswitch 122 causes a signal to pass through elapsed time reset register 124, in order to reset time elapsed display 108 and in order to reset RF output enable register 118. The resetting of RF output enable register 118 causes RF output enable gate 102 to turn off RF power supply 51. Debounce circuit 126 is provided for footswitch 122.

OPERATION

In operation of the embodiments of the invention described above, the user first preselects the desired therapeutic temperature (temperature set voltage 92, FIG. 12), and sets the length of time during which heating is to take place (time set switches 112, FIG. 12). The catheter, probe, or guidewire is inserted into the patient's body in a manner such that the electrode portion is in contact with the tissue to be heated. The user depresses footswitch 122 (FIG. 12) to initiate the heating between the electrode and the patient grounding plate. Heating will continue until the time set by the user has elapsed, or until the user deactivates footswitch 122. The tissue is heated by ohmic losses, with the heating being greatest in the immediate vicinity of the electrode. The control circuitry utilizes the feedback from the thermistor to regulate the heating process in order to ensure that the body tissue is not overheated. The circuitry thus prevents charring of the tissue, which can lead to a high impedance between the electrode and the grounding plate, and prevents sticking of the probe to the tissue. Consequently, the heating process can be predictable, prolonged, and uniform, and the heat can be allowed to penetrate deeply into the tissue.

Other embodiments are within the following claims. Medical devices other than those described above, such as a self-cauterizing scalpel blade that cauterizes tissue as it cuts the tissue, could incorporate the principles of the invention. The temperature sensing device need not necessarily be a thermistor, but could instead be a lower-signal device such as a thermocouple, because the RF current is turned off during sensing.

Other embodiments are within the following claims.
I claim:

1. A method of ohmic heating of tissue of a patient in order to induce coagulation, comprising the steps of
    selecting a temperature at which target tissue is to be coagulated through flow of RF current through tissue disposed between a thermally conductive, tissue-engaging electrode and at least one other patient-contacting RF conductor, said selected temperature being a maximum temperature consistent with avoiding detrimental sticking of the electrode to the tissue directly engaged by the electrode and avoiding undesired desiccation of tissue,
    repeatedly switching between a power on mode and a power off mode,
    during said power on mode, applying RF power to said electrode and said at least one other conductor in order to cause RF current of a frequency in the range of about 100 kilohertz to 100 megahertz to flow between said electrode and said at least one other conductor for tissue-coagulation, said thermally conductive, tissue-engaging electrode concentrating RF current in a local region of the patient's tissue in the vicinity of said electrode,
    during said power off mode, sensing, by means of a temperature sensor carried by and in thermally conductive relationship with said thermally conductive, tissue-engaging electrode, the temperature of said electrode in the absence of RF signal, thereby to sense indirectly the temperature of tissue contacted directly by the electrode, said temperature sensor having a greater accuracy in the absence of interfering RF electrical noise caused by said RF current passing through said thermally conductive electrode than in the presence of said interfering RF electrical noise, comparing said sensed temperature to said selected, maximum temperature, modulating said Rf power applied to said electrode in accordance with comparison of said sensed temperature and said selected, maximum temperature, and coagulating said target tissue at said selected, maximum temperature as said modulated RF current flows between said electrode and said at least one other conductor during said power on mode.

2. The method of claim 1 wherein said temperature sensor is a thermistor.

3. The method of claim 1 wherein the period of temperature sensing is of the order of 1 percent of the cycle time.

4. The method of claim 1 wherein said at least one other conductor is a patient grounding plate.

5. The method of claim 1 wherein said thermally conductive, tissue-contacting electrode and said at least one other patient-contacting RF conductor comprise opposed electrodes each of which has a localized contact with the tissue of said patient.

6. The method of claim 5 wherein said electrodes are mounted on opposing jaws of a forceps, and said method further comprises the step of grasping tissue between said opposing jaws of said forceps.

7. The method of claim 5 or 6 wherein said step of sensing temperature comprises sensing the temperature of each of said electrodes.

8. The method of claim 7 wherein said step of modulating said RF power is performed in accordance with the higher temperature sensed during said step of sensing the temperature of each of said electrodes.

9. The method of claim 1 wherein said temperature sensor comprises a thermocouple.

10. The method of claim 1 wherein said thermally conductive, tissue-engaging electrode is mounted on a gastro-intestinal hemostasis probe, said method further comprises the step of inserting said gastro-intestinal hemostasis probe into the gastro-intestinal tract of said patient, and said step of coagulating said target tissue comprises inducing gastro-intestinal hemostasis.

11. The method of claim 1 wherein said thermally conductive, tissue-engaging electrode is located on a surgical hemostasis probe, said method further comprises the step of applying said surgical hemostasis probe to the body of said patient at a location at which surgery is being performed, and said step of coagulating said target tissue comprises inducing hemostasis in the vicinity of said surgical probe.

12. The method of claim 1 wherein said thermally conductive, tissue-engaging electrode is located on a guidewire probe.

13. The method of claim 12 wherein
said electrode comprises a tip of said guidewire probe,
said guidewire probe is coated with insulation except at said electrode tip of said probe,
said thermistor is mounted within said tip of said guidewire probe
said method further comprises the step of inserting said guidewire probe into a duct in said patient's body, and
said step of coagulating said target tissue results in thermal occlusion of said duct.

14. The method of claim 13 wherein said duct is a seminal duct and said step of coagulating said target tissue results in thermal occlusion of said seminal duct.

15. The method of claim 13 wherein said duct is a fallopian tube and said step of coagulating said target tissue comprises thermal occlusion of said fallopian tube.

16. The method of claim 1 wherein said thermally conductive, tissued-engaging electrode is located on a needle.

17. The method of claim 16 wherein
said electrode comprises a tip of said needle,
said method further comprises the step of passing said needle through the skin of said patient,
and said step of coagulating said target tissue comprises percutaneously inducing coagulation treatment of a liver metastasis.

18. The method of claim 17 wherein
said electrode comprises a tip of said needle,
and said step of coagulating said target tissue comprises inducing coagulation treatment of a prostatic tumor.

19. The method of claim 1 wherein said thermally conductive, tissue-engaging electrode is mounted on a thermal ablation probe, said method further comprises the steps of sensing electrical impulses from the heart using at least one electro-physiology electrode mounted on said thermal ablation probe and positioning said electrode at the location of a source of arrythmia, and said step of coagulating said target tissue comprises inducing coagulation of said location of said source of arrythmia.

20. The method of claim 1 wherein
said step of applying RF power to said electrode and said at least one other conductor is performed by an RF power supply having one pole connected to said electrode and a second pole connected to said at least one other conductor,
and said steps of comparing said sensed temperature to said selected, maximum temperature and modulating said RF power applied to said electrode are performed by a control circuit connected to said temperature sensor and constructed to modulate RF power applied to said electrode according to the signal received from said temperature sensor.

21. The method of claim 1 wherein
said step of selecting said maximum temperature comprises setting a reference signal,
and said step of modulating said RF power to said electrode comprises causing said temperature of said electrode to approach a temperature represented by said reference signal, thereby to control the temperature of said electrode and consequently the temperature of tissue contacted by the electrode.

* * * * *

UNITED STATES PATENT AND TRADEMARK OFFICE
CERTIFICATE OF CORRECTION

PATENT NO. : 5,122,137

DATED : June 16, 1992

INVENTOR(S) : Charles D. Lennox

It is certified that error appears in the above-identified patent and that said Letters Patent is hereby corrected as shown below:

```
Col. 3, line 24, "3" should be --13--;
        line 43, delete "30".
Col. 5, line 1, "tot he" should be --to the--;
        line 18, after "ablation" insert --therapy--.
Col. 9, line 5, "Rf" should be --RF--.
```

Signed and Sealed this

Twelfth Day of October, 1993

Attest:

BRUCE LEHMAN

Attesting Officer

Commissioner of Patents and Trademarks